United States Patent [19]

Kurtz

[11] Patent Number: 4,513,154

[45] Date of Patent: * Apr. 23, 1985

[54] PROCESS FOR CONSECUTIVE COMPETITIVE GAS PHASE REACTION

[75] Inventor: Bruce E. Kurtz, Marcellus, N.Y.

[73] Assignee: Allied Corporation, Morris Township, Morris County, N.J.

[*] Notice: The portion of the term of this patent subsequent to Feb. 5, 1997 has been disclaimed.

[21] Appl. No.: 172,725

[22] Filed: Jul. 28, 1980

Related U.S. Application Data

[60] Continuation-in-part of Ser. No. 46,987, Jun. 8, 1979, abandoned, which is a division of Ser. No. 644,788, Dec. 29, 1975, Pat. No. 4,187,235, which is a continuation-in-part of Ser. No. 363,445, May 24, 1973, abandoned, which is a division of Ser. No. 167,733, Jul. 30, 1971, abandoned.

[51] Int. Cl.$^3$ .............................................. C07C 17/00
[52] U.S. Cl. ................................... 570/145; 570/147; 570/161; 570/170; 570/174; 570/196; 570/198; 570/200; 570/206; 570/208; 570/231; 570/234; 570/254; 570/255
[58] Field of Search ............... 570/255, 234, 254, 145, 570/147, 161, 170, 174, 191, 193, 196, 197, 198, 200, 206, 207, 208, 210, 231

[56] References Cited

U.S. PATENT DOCUMENTS

| | | | |
|---|---|---|---|
| 1,333,328 | 3/1920 | Martin | 422/202 X |
| 1,717,136 | 6/1929 | Ayres | 570/255 |
| 2,585,469 | 2/1952 | Johnson | 260/662 |
| 3,256,802 | 6/1966 | Karr | 261/99 X |
| 3,482,947 | 12/1969 | Jacobsen et al. | 422/202 X |
| 3,677,714 | 7/1972 | Ledgett | 422/198 |
| 4,187,253 | 2/1980 | Kurtz | 570/255 |

FOREIGN PATENT DOCUMENTS

| | | |
|---|---|---|
| 990738 | 6/1976 | Canada . |
| 127243 | 5/1926 | Switzerland . |

Primary Examiner—Charles F. Warren
Assistant Examiner—Joseph A. Boska
Attorney, Agent, or Firm—Thomas D. Hoffman

[57] ABSTRACT

A process for consecutive-competitive gas phase halogenation of organic compounds, i.e. alkanes, alkenes and benzene, alkyl benzenes and alkenyl benzenes containing labile hydrogens and having no more than 12 and 9 carbon atoms, respectively, in a thin reaction film on the surface of a porous barrier for production of highly halogenated products by substantial suppression of diffusion of partially halogenated intermediates away from the reaction film is disclosed.

21 Claims, 13 Drawing Figures $c_m$ = CONCENTRATION OF COMPONENT $AX_{4-n}Y_n$ IN THE BULK PHASE.

$c'_m$ = CONCENTRATION OF COMPONENT $AX_{4-n}Y_n$ IN THE REACTION FILM.

PRODUCT COMPOSITION FOR CONSECUTIVE-COMPETITIVE REACTIONS IN A POROUS TUBE REACTOR IN MODERATELY-DEVELOPED LAMINAR FLOW (R = 9)

($K_1 = K_2 = K_3 = K_4 = K_5 = K_6 = K_7 = 1$)

PRODUCT COMPOSITION FOR CONSECUTIVE-COMPETITIVE REACTIONS IN A POROUS TUBE REACTOR IN FULLY-DEVELOPED LAMINAR FLOW
($R = 99$)

($K_1 = K_2 = K_3 = K_4 = K_5 = K_6 = K_7 = 1$)

SCHEMATIC DEPICTION OF THE
REACTIONS OCCURING IN THE
VICINITY OF THE POROUS WALL
(NOT TO SCALE)

PROCESS FOR CONSECUTIVE COMPETITIVE GAS PHASE REACTION

DESCRIPTION

Cross-Reference to Related Application

This application is a continuation-in-part of copending application U.S. Ser. No. 046,987, filed June 8, 1979, abandoned which is a divisional application of U.S. Ser. No. 644,788, filed on Dec. 29, 1975 and now U.S. Pat. No. 4,187,235 issued on Feb. 5, 1980, which is a continuation-in-part of application U.S. Ser. No. 363,445, filed May 24, 1973, and now abandoned, which is a divisional application of U.S. Ser. No. 167,733, filed July 30, 1971 now abandoned.

BACKGROUND OF THE INVENTION

1. Field of the Invention

This invention relates to process for consecutive, competitive gas phase halogenation of gaseous aliphatic and aromatic hydrocarbons of no more than 12 and 9 carbon atoms, respectively and their partially reacted intermediates. More specifically, it relates to a process for the suppression of partially substituted intermediates in consecutive-competitive gas phase reactions to produce various commercially desirable halogenated derivatives, economically and in high yield.

2. Description of the Prior Art

Halogenated derivatives of hydrocarbons are widely employed in the industry in a variety of applications, including such uses as solvents and intermediates in the production of refrigerants and other chemicals. However, production of these halogenated derivatives from hydrocarbons, their partially halogenated derivatives and mixtures thereof by first order, consecutive-competitive reactions with a gaseous halogen is complicated by the formation of undesired by-products, e.g. partially halogenated intermediates. When tubular flow and back-mix reactors are employed in the chlorination of methane and partially-chlorinated derivatives thereof, relatively high amounts of undesired partially-chlorinated by-products have been found to be produced at the expense of the desired carbon tetrachloride. In the chlorination of ethane and partially-chlorinated ethanes, relatively high amounts of undesired chloroethanes have been found to be produced at the expense of the desired chloroethylenes. Moreover, since these chlorination reactions are exothermic, conventional reactors are disadvantaged by the practical limits placed on the rate of chlorine fed to the reactor due to difficulty in removing the heat of reaction and, hence, in controlling the reaction temperature. Excessively high temperatures are not desired because they result in formation of large amounts of carbon, due to pyrolysis of the hydrocarbon feed, which fouls the reactor and downstream equipment. Thus, the prior art has typically employed staged reactions (to provide incremental reaction of the hydrocarbon and chlorine), with intermediate cooling or with extensive recycle of less highly chlorinated by-products in order to obtain the desired chlorinated hydrocarbon. Use of staged reaction methods or of extensive recycles is undesirable because of the large amount of equipment required and the consequent high cost.

SUMMARY OF THE INVENTION

A process for suppression of partially halogenated intermediates in consecutive competitive gas phase reaction is provided which comprises:

a. passing a first gas feed stream containing carbon compounds having labile hydrogens selected from the group consisting of straight and branched chain cyclic and acyclic alkanes and alkenes having no more than 12 carbon atoms, benzenes, alkylbenzenes and alkenylbenzenes having no more than 9 carbon atoms, their partially reacted intermediates and mixtures thereof under pressure into one end of a first elongated gas zone positioned within a substantially gas-impervious barrier;

b. passing a second gas stream containing a member selected from the group consisting of $F_2$, $Cl_2$, and $Br_2$ under pressure into a second elongated gas zone positioned along said first zone, said first and second elongated gas zones being separated along the major length thereof by a porous member;

c. maintaining the pressure of the second gas stream in the second gas zone in excess of the pressure in the first gas zone to allow flow of said second gas through the porous member;

d. maintaining a Reynolds number, $N_{Re}$, in the first gas zone at a non-zero value less than 2,000 to effect consecutive-competitive reaction between the first gas and the second gas for formation of a halogenated product in a reaction film on the surface of the porous member facing the first zone and to suppress diffusion of partially halogenated intermediates from said reaction film wherein the Reynolds number, $$N_{Re} = \frac{4A\bar{v}\rho}{P\mu}$$

wherein
A = cross-sectional area of the first gas zone:
P = length of the perimeter of the cross-sectional area of the first gas zone;
$\bar{v}$ = average velocity of the gas stream in the first gas zone;
$\rho$ = density of the gas stream in the first gas zone;
$\mu$ = viscosity of the gas in the first gas zone; and e. withdrawing a gas stream containing the halogenated product from the other end of the first gas zone.

BRIEF DESCRIPTION OF THE DRAWINGS

Preferred embodiments of the apparatus of the present invention are illustrated in the accompanying drawings wherein.

The particulars of the method of constructing the apparatus of the present invention which are not specified herein are considered to be within the knowledge of a reasonably skilled workman in the art.

DETAILED DESCRIPTION OF THE INVENTION

Figure 11:
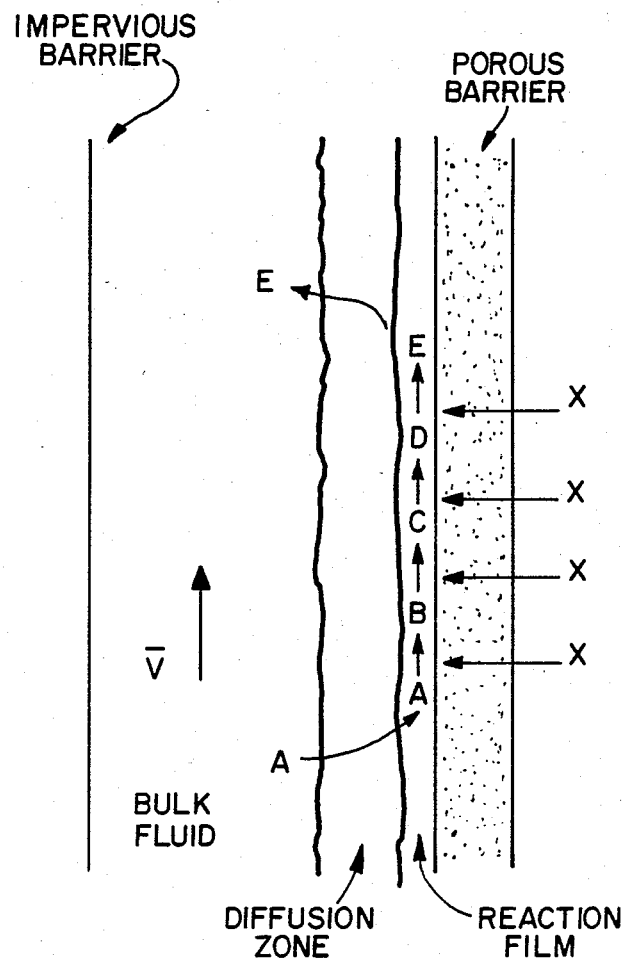
FIG. 11 is a schematic of the reactions occurring in the vicinity of a porous barrier.

The process of the present invention is better understood by reference to FIG. 11.

FIG. 11 depict the reaction of A with X to form intermediate product B which can further react with X to form C. This reaction sequence can continue to form completely reacted product E in the chlorination of methane. A represents methane, X represents chlorine, and B,C,D, and E represent $CH_3Cl$, $CH_2Cl_2$, $CHCl_3$, and $CCl_4$, respectively. These reactions occur in a thin reaction film in the immediate vicinity of the porous tube surface. Reactant A enters the reactor and flows parallel to the porous tube. A fraction of it can diffuse to the porous tube. The local concentration of X is quite high in the thin reaction film on the outside wall of the porous tube. If the rate of reaction is sufficiently fast that the consecutive reactions occur before B,C, and D have a chance to diffuse away from the reaction film, then the reaction product will substantially be the fully reacted product E. It is essential that the zone through which the products diffuse be fairly thick to insure that fully reacted products dominate. This will occur if the flow of the reactants and products in the space between the porous and impervious tubes is laminar. Laminar flow implies that the motion of molecular perpendicular to the direction of flow is due to diffusion and not to bulk flow. Turbulent flow, on the other hand, would lead to greatly increased mixing of the reactants due to fluid motion. This would shrink the diffusion zone and favor the formation of partially reacted species since they would be removed from the reaction film before the reaction sequence had been completed.

The conditions under which laminar or turbulent flow will occur is determined by the nature of the reactant and, product physical properties, the flow rates and the reactor geometry. In accordance with the process of the present invention, it was discovered that by maintaining Reynolds number, $N_{Re}$, for the gas stream in the elongated gas passage bounded by a substantially gas impervious barrier and a porous barrier, preferably in an annular space bounded by a substantially gas-impervious outer barrier and an inner porous tube, at a non-zero value less than about 2,000, the consecutive-competitive reaction between the first gas stream containing organic compounds having no more than 12 carbons and containing labile hydrogens and the second stream containing halogen in the thin reactor film on the outer surface of the porous barrier proceeds to produce more highly halogenated organic compounds and the diffusion of partially halogenated intermediate products away from the reaction film is substantially suppressed.

For example, isobutylene was reacted with chlorine in a porous (ALUNDUM ®) tube reactor in the presence of a $CuCl_2$ catalyst in accordance with the process of the present invention. A high percentage of penta- and hexa-chloroisobutylenes was recovered. Less highly chlorinated products and cleavage products were suppressed.

If the Reynolds number is above about 2000, the flow in the first reaction zone will become turbulent and the mixing of the gaseous reactants will be greatly increased. The diffusion of partially halogenated intermediates away from the reaction film will no longer be substantially suppressed and production of the highly desirable more fully halogenated organic compounds will be lower.

The Reynolds number, as defined below, can be determined for flow in a reaction zone of any geometry. The general form of the equation is $$N_{Re} = \frac{4A\bar{v}\rho}{P\mu} \quad \text{(Eqn a)}$$

where A is the cross-sectional area of the reaction zone, P is the length of the perimeter of the cross-sectional area, $\bar{v}$ is the average velocity of the gas stream in the first gas zone, $\rho$ is the density of the gas stream in the first gas zone and $\mu$ is the viscosity of the gas stream in the first gas zone. In the preferred embodiment of the present invention, the first gas zone is annularly shaped zone and $N_{Re}$ is defined as follows:

$$N_{Re} = (D - d)\frac{\bar{v}\rho}{\mu} \quad \text{(Eqn b)}$$

where D is the inner diameter of the gas impervious tube, d is the outer diameter of the porous tube and $\bar{v}$, $\rho$ and $\mu$ are the same as defined above. For proper operation of the process of the present invention, the values for $\bar{v}$ are from about 0.1 to about 30,000 cm/sec, usually 0.1 to 2000 cm/sec³. The values for $\rho$ are from about 0.0005 to 1 g/m³; usually from about 0.001 to about 0.1 g/cm³; and the values for $\mu$ are from about $70 \times 10^{-6}$ g/cm-s usually from about $70 \times 10^{-6}$ to $500 \times 10^{-6}$ g/cm-s.

Alternatively, the Reynolds number can be defined in terms of total volumetric flow of the material in the annular space, i.e. V and the cross-sectional area of the annular space, i.e. A. The equation for the Reynolds number would then be as follows:

$$N_{Re} = (D - d)\frac{V\rho}{A\mu} \quad \text{(Eqn c)}$$

Proper operation of the process of the present invention requires that the Reynolds number be maintained at a non-zero value less than about 2000. Substituting a value of 2000 into Eqns b and c and rearranging the terms leads to the following expressions which specify the proper criteria for substantial suppression of diffusion of the partially halogenated reaction intermediates away from the thin reaction film on the surface of the porous tube in the annular space:

$$(D + d) > \frac{0.002}{\pi} \frac{V\rho}{\mu} \quad \text{(Eqn d)}$$

and $$(D - d) < 2000 \frac{\mu}{v\rho} \quad \text{(Eqn e)}$$

Satisfying these equations will allow the diffusion zone (FIG. 11) to form and thus suppress the build-up of the partially halogenated intermediates.

Figure 12A:
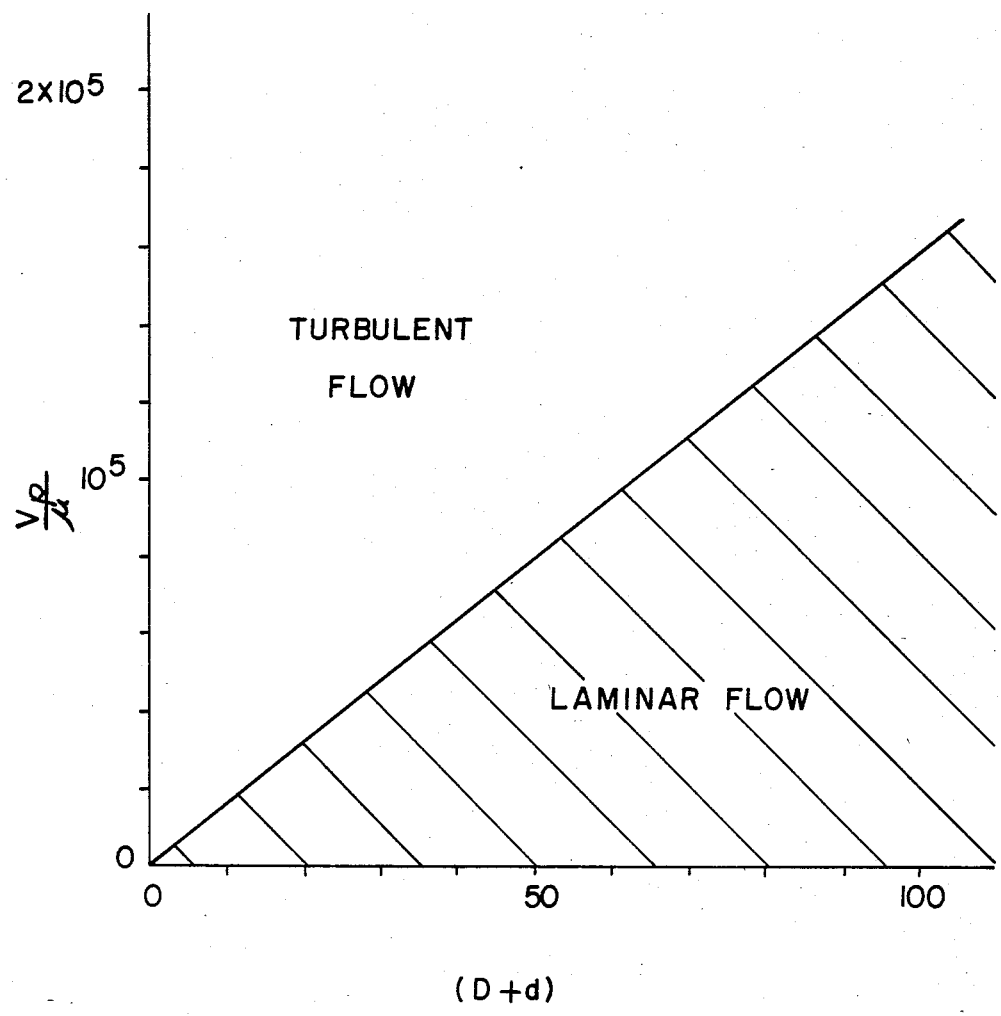
FIGS. 12a and b are plots of gas flow parameters vs. reactor dimensions for phase phase reactions in laminar and turbulent flow.
Figure 12B:
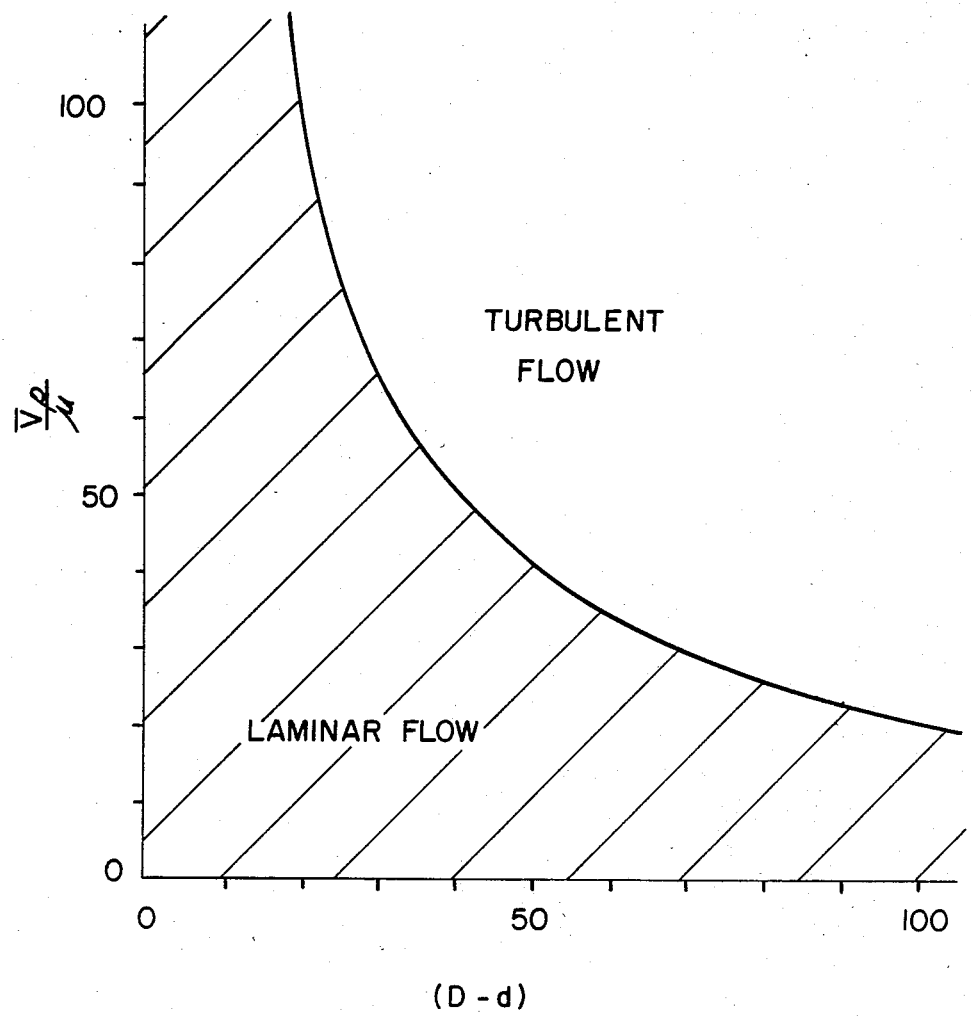

The regimes in which laminar flow is expected to occur is depicted graphically as shown in FIG. 12A (Eqn d) and in FIG. 12b (Eqn e). The hatched areas are the laminar regions. Thus, knowing the viscosity and density of the fluid in the reactor and the mean velocity or total flow rate of the reactants, a range of reactor dimensions can be calculated which will ensure that the flow will be laminar.

As an example, consider a porous tube reactor in which V=2 1/sec, $\rho$=1.5 g/l, $\mu$=0.00015 g/cm-sec. These fluid properties are typical of reactants comprising a gaseous hydrocarbon and chlorine or fluorine at atmospheric pressure and an elevated temperature. Substituting these values into Equation d leads to (D+d)>40/$\pi$. If the diameter of the porous tube, d, is 3 cm, then the inner diameter D of the impervious tube must be at least 9.7 cm. If D were reduced to 4 cm, then $N_{Re}$ would be 3638 and the flow turbulent. If D were 16 cm, $N_{Re}$ would be 1340 and the flow laminar. It can be verified that these conditions fall outside and inside the hatched area of FIG. 12a.

An example using either Equation e or FIG. 12b follows. Assume a mean velocity through a cross-section of the annular space to be 50 cm/s. Using a fluid with the same physical properties as above, (D-d) can be calculated to be smaller than 4 cm in order to have laminar flow. Thus, if (D-d) is 2 cm, the Reynolds number would be 1000 and the flow laminar. If (D-d) is 10 cm, it would be 5000 and the flow turbulent.

Adjustment of the flow of gas in the annular space is considered to be within the skill of the ordinary artisan in the field.

The first gas stream contains a carbon compound having labile hydrogens selected from the group consisting of straight and branched chain cyclic and acyclic alkanes and alkenes having no more than 12 carbon atoms, benzenes, alkyl benzenes and alkenylbenzene having no more than 9 carbon atoms, their partially reacted intermediates and mixtures thereof.

Among the compounds found useful for the process of the present invention are straight and branched chain cyclic and acyclic alkanes and alkenes having no more than 12 carbon atoms such as methane, ethane, ethene, propane, propene, n-butane, isobutane, 2-methyl-1-butene, isobutylene, n-pentane, isopentones, 1-pentene, 2-pentene, 3-pentene, 2-methylpentene-1, 2-methylpentene-2, neopentane, cyclopentane, n-hexane, iso-hexanes, 1-,2- and 3-hexenes, iso-hexene, 2-ethylhexane, cyclohexane, cyclohexene, n-heptane, isoheptane, tert-heptane, 1-,2-,3- and 4-heptenes, 1-,2- and 3-methyl-heptanes, n-octane, iso-octane, 1-,2-,3- and 4-octenes, 1-,2-,3- and 4-methyl-octanes, n-nonane, isononane, isomeric nonenes, n-decane, iso-decane, isomeric nonenes, n-undecane iso-undecanes, isomeric-undecenes, n-dodecane, iso-docecane, isomeric decenes and similar compounds. Partially halogenated derivatives of the compounds listed above are also considered within the scope of the present invention.

The temperature of the halogenation process of the present invention can vary from room temperature to no more than about 500° C. While fluorinations can be effected at room temperature higher temperatures are required for chlorination, e.g. 250°–500° C. The higher temperature ranges are usually employed for halogenation of benzene, alkyl and alkenyl benzenes. Of course, the lower limit of the temperature range can be employed for the straight and branched chain alkanes and alkenes so long as their boiling points are exceeded. Temperature can be selected to favor substitution over addition to carbon-carbon double bonds.

As is well known in the art, a catalyst is usually employed for carbon compounds having 3 to 12 carbon atoms. See Example 6 wherein $CuCl_2$ is employed in the chlorination of isobutylene.

The porous tubes can be constructed of any material which is inert to the gaseous reactants and products.

The halogens, $F_2$, $Cl_2$ and $Br_2$ of course must be in the gaseous form.

The amount of halogen introduced is approximately equal to the amount of halogen required to convert at least 50% of the labile hydrogens into carbon-halogen bonds. One mole of halogen is required per mole of labile hydrogen to form a carbon halogen bond and hydrogen halide.

While the present invention is generally useful for the consecutive-competitive gas phase halogenation of carbon compounds containing labile hydrogens and having no more than 12 carbon atoms, the chlorination of hydrocarbons having from 1 to 2 carbon atoms will be discussed below.

Exemplary of a process of the present invention is the isothermal chlorination of a feed stream selected from the group consisting of hydrocarbons having from 1 to 2 carbon atoms, their partially chlorinated derivatives and mixtures thereof, to form chlorinated derivative thereof is disclosed; the process comprises (a) passing a gas containing the feed stream under pressure into a first elongated gas zone, (b) passing a gas containing chlorine under pressure into a second elongated gas zone positioned along said first gas zone, said first and second elongated gas zones being separated by a porous member, (c) maintaining the pressure of the gases in said second gas zone in excess of the pressure in said first gas zone, (d) maintaining said first gas zone under conditions sufficient to effect reaction therein of at least a portion of said diffused chlorine with the feed stream for production of the desired chlorinated derivatives, and (e) withdrawing the gas product containing the desired chlorinated derivatives from said first gas zone.

A specific process of the present invention provides reaction between the chlorine and the feed stream in the first gas zone as the feed stream flows longitudinally therethrough, while the gas containing chlorine diffuses thereto through the porous member which separates the two gas zones. The first gas zone may be equipped with cooling means so as to remove the heat generated by the reaction of chlorine and the feed stream.

The present invention has been found to allow use of increased chlorine-to-feed stream ratios to provide substantially complete conversion of the feed stream in the reactor, thereby eliminating the need for staged reactions with intermediate cooling or extensive recycle of less highly chlorinated by-products or unreacted gases. Moreover, the present invention has been found to markedly reduce the formation of by-products at a given chlorine-to-feed stream ratio and temperature, thereby reducing or eliminating the need to separate less highly chlorinated by-products from the product stream. Further, the desired reactions have been found to proceed at lower temperatures, thus providing concomitant savings in heat requirements and in increased equipment life.

With respect to the chlorination of methane, substantially complete suppression of intermediate products has been found to result from operation of a preferred embodiment of the process of the present invention wherein the flow of the gas through the first elongated gas zone is maintained in the laminar region.

In the process of the present invention, it is essential that the mixing of the two gaseous reactants in the annular space be severely restricted. In the prior art, for example U.S. Pat. No. 1,333,328 (Martin), porous elements were used to increase the mixing to provide more intimate contact between the two reactants. However, the process of the present invention restricts mixing in the annular space by maintaining the Reynolds number for gas stream in the annular space below 2000 so as to allow for production of more highly halogenated products formed by consecutive-competitive reaction between the halogen and organic compounds having labile hydrogens in the thin reaction film on the surface of the porous tube and to suppress diffusion of partially halogenated intermediate reaction products away from the thin film.

In the prior art chlorine and hydrocarbon reactants are conventionally introduced to a tubular flow or back-mixed reactor at the same point, so that the rate of chlorination reaction is initially at a maximum, decreasing as the amount of free chlorine is depleted in the reaction chamber. If the reaction is strongly exothermic (as is generally the case for these chlorination reactions) the rate of heat evolution is initially very large. In the case of a tubular flow reactor surrounded by a cooling medium, the temperature will rapidly rise to a maximum near the feed end of the reactor and gradually decrease toward the exit end as the chlorine reactant is exhausted. Thus, while chlorine to methane molar feed ratios approaching 4.0 would provide a gas containing close to 100 mole percent carbon tetrachloride, this temperature rise imposes a practical upper limit on the molar ratio of chlorine to hydrocarbon in the feed, typically about 0.25, so that staged introduction of chlorine and intermediate cooling are required, an expensive and wasteful use of alternate heating and cooling means. In contrast, in the process of the present invention, the reaction rate is substantially uniform along the length of the elongated reaction zone, providing a uniform rate of heat evolution and, with the provision of suitable cooling means, allowing obtainment of essentially isothermal conditions in the reaction zone, removing the need to employ staged chlorine addition and interstage cooling.

Chlorination in the apparatus of the present invention has additional advantages over conventional methods. Exceptionally high yields are obtained per pass, and the uniform rates of heat evolution and use of suitable cooling means leads to essentially isothermal operation, thus preventing pyrolysis of the feed stream, so that, consequently, virtually no carbon is formed to foul the reactor and downstream equipment.

The apparatus of the present invention for halogenation of 1 and 2 carbon hydrocarbons, their partially chlorinated derivatives and mixtures thereof, comprises, in its broadest sense, an elongated housing provided with first and second elongated gas passages disposed therein. These passages are positioned substantially along one another and are separated by a porous member, for the major portion of their length, so that the desired gases may pass from the second passage into the first passage along the major portion of the length of these elongated gas passages. The shape of the cross-section of the elongated first and second gas passages is not critical, and thus, these passages may be rectangular, circular or assymmetrical. However, it is preferred that first and second gas passages be cylindrical, and hence of a circular cross-section.

In the preferred embodiment, the apparatus of the present invention for chlorination of 1 and 2 carbon hydrocarbons, their partially chlorinated derivatives and mixtures thereof, comprises an elongated porous tube having an elongated gas zone disposed therein, and provided with gas inlet means for passing gas into said elongated gas zone; and outer elongated tube provided with substantially gas-impervious outer walls surrounding the porous tube and adapted to define an elongated annual gas zone internal to the outer tube and external to the porous member; means for introducing gas into the annular gas zone at a rate such that the flow of gas through said first gas passage is in the laminar region; means for maintaining the pressure in the elongated gas zone internal to the porous tube in excess of the pressure in the annular gas zone for diffusion of gas from the elongated gas zone into the annular gas zone, and outlet means for discharging gas from the annular gas zone. Heat exchange means for controlling the temperature within the annular gas zone may also be provided.

Most preferably, the elongated porous tube is open at one end and closed at the other. Thus, in the preferred embodiment of the apparatus of the present invention a chlorine-containing gas under pressure is passed into an elongated inner zone provided in an elongated porous tube closed at one end and open at the other end; a gas containing the feed stream of hydrocarbons having from 1 to 2 carbon atoms, their partially chlorinated derivatives and mixtures thereof is passed through an elongated annular reaction zone surrounding the porous tube; the pressure in said inner zone is maintained in excess of the pressure in said annular reaction zone for diffusion of chlorine-containing gas through said porous tube; said diffused chlorine-containing gas is reacted with said feed stream in said annular reaction zone; and the reaction product mixture is discharged from said reaction zone. In such an embodiment, the present invention would provide reaction between the chlorine and the feed stream in the annular space surrounding the porous axial core as the hydrocarbon reactant diffuses radially from a porous axial core.

The apparatus of the present invention herein referred to as a porous tube reactor may be used as a single unit. Alternatively, one or more serially arranged units, or a plurality of unit reactors arranged for parallel operation, may be employed. In the preferred embodiment, a single unit of the porous tube reactor of the present invention comprises two concentric tubes with the inner tube being preferably closed at one end and being provided with a porous wall and an inlet for introducing a reactant gas therein. The outer tube is positioned about the inner tube to provide an annular space longitudinally therebetween and is provided with an inlet for an outlet for the gas reaction product. Optionally, heat transfer means can be associated with the outer tube.

In use, a gas mixture containing chlorine, preferably as molecular chlorine, is introduced into the inner tube and is diffused radially, and preferably substantially uniformly, into the annulus defined by the inner and outer tubes, reacting therein with a gas containing the hydrocarbon reactant introduced into the annulus. The reaction product is removed from the annulus through the outlet thereof, which outlet is generally positioned at a point removed from the inlet of the annulus. The reactor of this invention is specifically designed for isothermal reaction temperatures and therefore the design is such that the reaction takes place in the annulus where the temperature control to assure thermal conditions is possible. In addition to temperature control, the system, of which this reactor is a part, is also designed for careful control of such variables as flow rate, proportion of reactants, residence time, and importantly, the degree of mixing in the annulus.

In the event a plurality of unit reactors is employed, they may be arranged for parallel operation in an outer casing with inlet and outlet ports, so that a heat transfer medium may circulate within the outer shell or jacket around the outer tubes of the plurality of units. Such an apparatus can be fabricated, for example, with a plurality of porous tube reactors spaced longitudinally within a containing casing.

Reference is now made to the accompanying drawings wherein like numerals indicate like or corresponding parts throughout the several views.

Figures 1, 2:
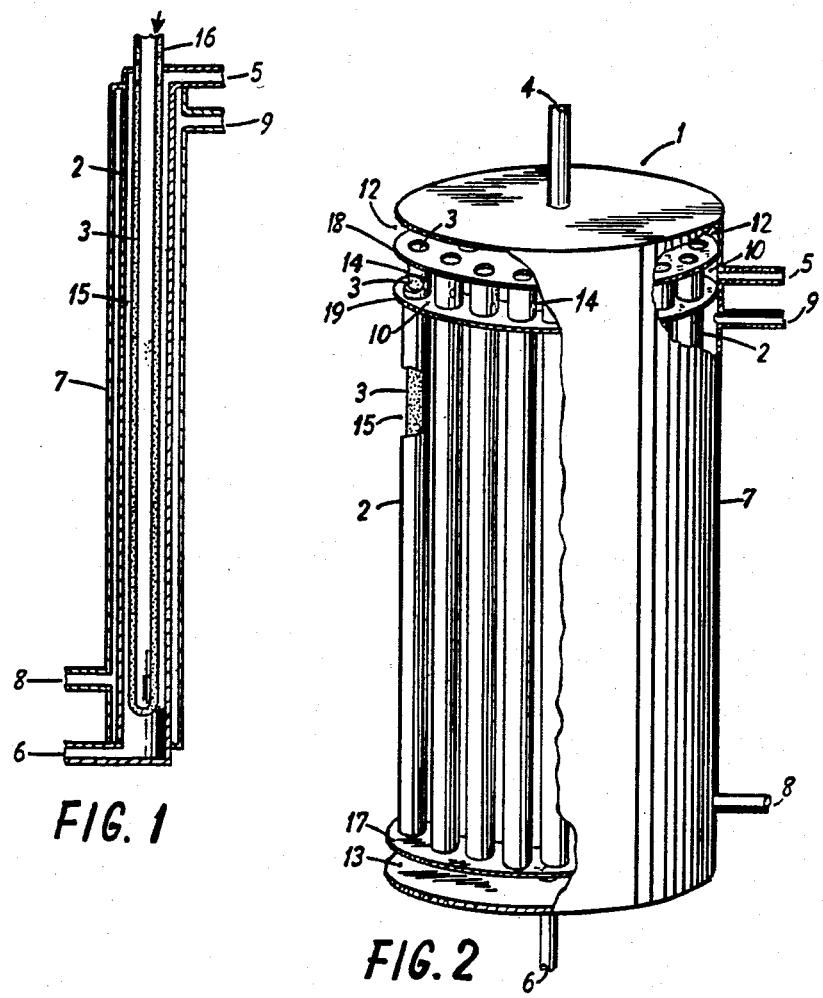
FIG. 1 is a longitudinal half section of one embodiment of the preferred apparatus of the present invention.
FIG. 2 is a perspective break-away view illustrating a preferred embodiment wherein a plurality of porous tube reaction units are combined for parallel action.

Referring to the porous tube reactor of FIG. 1, a plurality of which are also shown in the assembly of FIG. 2, the individual reactor comprises an outer tube 2, which is substantially gas impervious, an inner porous tube 3, a feed inlet 4 for the gas containing chlorine, an inlet 5 for the feed stream containing the selected hydrocarbon reactant, a product outlet 6, and optionally, a jacket 7 for a heat transfer medium, said jacket having an inlet 8, and an outlet 9 for the heat transfer medium. The unit and the assembly comprising a plurality of these units should be resistant to chlorine and to HCl gas and the organic and chlorinated organic gases which may be formed as by-products or employed as starting materials.

FIG. 2 illustrates a preferred embodiment of the present invention wherein a bundle of porous tube reactor units are arranged in parallel, in this instance in a cylindrical container. There are several ways this arrangement can be effected. In the method illustrated, there are two tube sheets, 18 and 19, at the upper end of the assembly and one tube sheet 17 at the lower end. These tube sheets are sealed along their periphery to the inner surface of the casing 7 to form two compartments or vestibules, 10 and 12, at the upper end of the assembly and one vestibule 13 at the lower end of the assembly. The outer impervious tubes are sealed into the bottom tube sheet 17 in the usual manner so that they then communicate with vestibule 13. The upper ends of these impervious tubes pass through and are sealed into tube sheet 19. The tubes then terminate at tube sheet 18, being sealed against the lower surface of the latter tube sheet. Since they are sealed to undersurface of tube sheet 18, the tubes do not communicate with vestibule 12 but surround the porous tube 3 which does so communicate. At least one opening, 14, is made in the impervious tube with the distance between tube sheet 18 and 19. With this arrangement, vestibule 12 is then in communication with vestibule 10 when one includes in the route of communication, the pores of the respective porous tubes. The short section of porous tube extending between tube sheets 18 and 19 is preferably rendered impervious as is also section 16 of the porous tube of FIGS. 1 and 3, and section 16a of the porous tube of FIG. 3.

Figure 3:
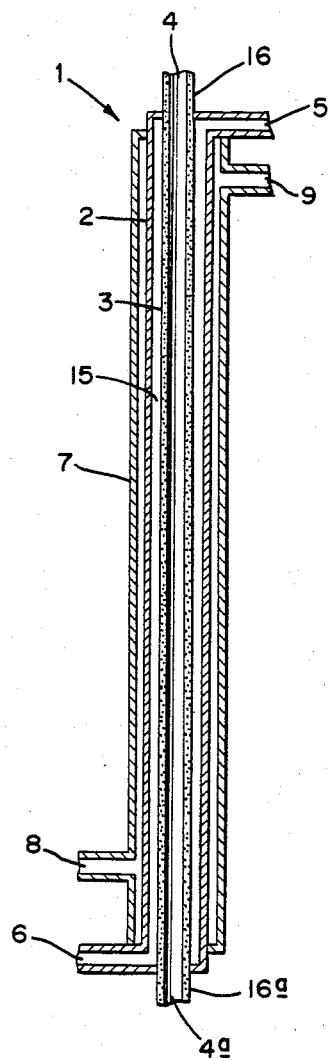
FIG. 3 is a longitudinal half section of a second embodiment of the preferred apparatus of the present invention.

In operation, a heat transfer medium such as molten sodium nitrate is introduced through inlet 8 of FIG. 1, and after circulating around impervious tube 2 exits at outlet 9. In the case of FIG. 2, there are no individual jackets surrounding impervious tubes 2 in FIG. 1. Such individual jackets are not necessary as the heat transfer medium enters the casing at inlet 8, circulates about all impervious tubes 2 and then exits at outlet 9. With respect to both FIG. 1 and FIG. 2, the gas containing chlorine is introduced at inlet 4 and the hydrocarbon feed stream is introduced at inlet 5. In the embodiment of FIG. 3, the gas containing chlorine is introduced to porous tube 3 at inlet 4 and that portion of this gas which does not pass through the porous walls into reaction zone 15, exits porous tube 3 at outlet 4a. In FIGS. 1 and 3 the gas containing chlorine diffuses substantially uniformly through porous wall 3 to react with the hydrocarbon in annular zone 15 between porous tube 3 and impervious tube 2. Because of the substantially uniform introduction of the gas containing chlorine throughout the full length of the porous tube and the application of a heat transfer medium to the exterior wall of tube 2 to initiate the reaction and to supply or extract heat as required, essentially isothermal reaction conditions in reaction zone 15 can be readily maintained if desired. The reaction product is removed from zone 15 through outlet 6. If desired, a portion of this reaction mixture may be recycled for further chlorination. In the apparatus of FIG. 2, a novel arrangement prevents the premature reaction between a portion of the reactants in vestibule 10. The hydrocarbon feed stream entering vestibule 10 does not enter the impervious tubes at their intersection with tube sheet 19, but rather through perforations 14 in the side of the tubes. To further eliminate any opportunity for a portion of the reaction to occur within vestibule 10, that portion of the porous tube which extends between tube sheets 18 and 19 is rendered impervious.

In connection with the operation of the multitube reactor as illustrated in FIG. 2, it should be noted that the preferred construction minimizes the possibility of the chlorine and hydrocarbon feed stream mixing in vestibule 10 and reacting. It will be noted that in the preferred embodiment the length of the porous tube passing between the tube sheets 18 and 19 is impervious and that the hydrocarbon feed stream entering the vestibule 10 at inlet 9 only enters the annulus through one or more openings in each tube, shown at 14, thus as the chlorine first diffuses through the tube it enters the heated section of the annulus where it reacts and does not escape into the vestibule.

The porous members separating the first and second gas passages in the apparatus of the present invention may be made of a wide variety of materials of construction. Vycor or quartz are quite satisfactory as materials of construction, although porous members made from alumina are preferred especially for large-scale operation. Thus, for example, porous alumina, ceramic tubes or even a sintered metal tube, where compatible, may be used as porous tube 3 in the apparatus illustrated in FIG. 1. A fritted Pyrex glass tube may also be employed. The purpose of the pores is to produce a substantially uniform diffusion of chlorine into the first gas zone for reaction with the hydrocarbon feed stream, thus enhancing high yields of the desired chlorinated hydrocarbon product. Thus, it is preferred that the porosity of the porous member be substantially uniform along its length. The average pore diameter of the pores in the porous member may vary from greater than about 0.5 up to about 1000 microns, with a range of from about 5 to 300 microns being preferred. While porous members having an average pore size of less than 0.5 microns may be used, the pressure required for diffusion of gases therethrough make use of such low porosites undesirable.

For simplicity of construction it is preferred that inner zone 4 in porous member 3 be substantially cylindrical and be of a uniform cross-section, although such uniformity in cross-section is not critical. While porous tube 3 is closed at one end and open at the other end in the preferred embodiment, as shown in FIG. 1, this is not critical, and a porous tube may be employed which is open at both ends, provided the gas containing the hydrocarbon passing longitudinally out of inner zone 4 in such an embodiment does not pass into the annular reaction zone. FIG. 3 illustrates such an embodiment, wherein the gas containing chlorine flows through porous tube 4 as indicated with recycle of non-diffused gases exiting outlet 4a. Moreover, in the embodiment of FIG. 3, the hydrocarbon feed stream can be fed to the core elongated zone 4 with the chlorine gas being fed to annular zone 15 at a greater pressure than is maintained in zone 4 for diffusion of chlorine from annular zone 15 into zone 4 for reaction with feed-stream therein. In such an embodiment, the roles of annular zone 15 and inner zone 4 are reversed with the latter zone now comprising the reaction zone, from which product is withdrawn at exit 4a. Nondiffused chlorine may thus be withdrawn via line 6 and recycled to annular zone 15 via line 5.

To provide higher conversions to the desired product, it is preferred that the apparatus of the present invention be characterized by a length-to-diameter ratio of at least about 3:1, and more preferably at least 10:1. As used herein, the length-to-diameter ratio is defined as the ratio of (1) the inside length of the first elongated gas zone wherein the chlorination reaction is effected, to (2) the average cross-sectional diameter of the first elongated gas zone. In the instance in which a porous tube reactor is employed, such as illustrated in FIG. 1, the inside length and inside diameter of outer tube 2 is used to compute this ratio.

The one and two carbon hydrocarbons which may be treated in the apparatus of the present invention are methane, ethane, ethylene and saturated and unsaturated partially chlorinated derivatives thereof, and mixtures of the above. Partially chlorinated derivatives of the foregoing one and two carbon hydrocarbons include methyl chloride, methylene chloride, trichloromethane, and chloroethylenes (mono-, di-, tri- and tetrachloroethylene), and the partially chlorinated ethanes, e.g. 1-chloroethane, 1,2-dichloroethane, 1,1-dichloroethane, 1,1,2-trichloroethane, 1,1,1-trichloroethane, 1,1,2,2-tetrachloroethane, and pentachloroethane. The precise chlorinated hydrocarbon or mixtures of chlorinated hydrocarbons obtained as product will, of course, depend on the hydrocarbon or mixture of hydrocarbons selected as starting material. Thus, while the present invention is particularly adapted to high yield production of carbon tetrachloride by controlled isothermal chlorination of methane, and production of methylchloroform, trichloroethylene and tetrachloroethylene by the controlled isothermal chlorination of ethane, a wide variety of product mixtures containing other chlorinated hydrocarbons can also be obtained.

To initiate the reaction and to maintain the desired temperature conditions throughout the chlorination, a heat transfer medium, appropriate to the chlorination being carried out, is circulated around the outer tube. In the equipment shown, this heat transfer medium enters inlet 8 and is discharged via outlet 9. By adjusting the temperature of this circulating medium, employing techniques known to the art, the temperature of the chlorination reaction may be maintained within the range of 250° to 500° C., preferably between 300° to 450° C., or desirably between 325° to 375° C. A suitable heat transfer medium is molten sodium nitrate or molten lead.

The molar ratio of the chlorine feed to the hydrocarbon feed will vary widely depending on the hydrocarbon fed, the product desired, and other factors. For example, the chlorine:methane molar feed ratio and the chlorine:ethane molar feed ratio will generally range from about 0.5:1 to about 5:1. However, higher or lower ratios can be employed.

The pressures employed in the first and second elongated gas zones (i.e., annular zone 15 and inner zone 4 in the apparatus of FIG. 1) are not critical and may vary widely. Thus, while pressures of from atmospheric to about 20 psig may be selected for ease of operation, pressures outside this range may also be used. However, to ensure diffusion of chlorine gas to zone 15, the pressure within inner zone 4 is maintained in excess of the pressure in annular zone 15. The pressure within the second elongated gas zone (inner zone 4) typically will be generally from about 0.2" Hg greater than that within the first elongated gas zone (annular zone 15) in order to assure flow of the chlorine containing gas through the porous wall.

While the following theory of operation should not be considered limiting in any way, it is believed that the desired chlorination reaction should be substantially confined to the surface of the porous tube to suppress formation of undesired by-products, e.g. methylene chloride and chloroform in the case of the chlorination of methane to produce carbon tetrachloride. Moreover, in the case of the chlorination of methane to form carbon tetrachloride, it is important for the rate of the competitive, consecutive reaction of the methane and its chlorinated derivatives with chlorine to form carbon tetrachloride to be fast compared to the rate of diffusion of the methane and chlorinated intermediates between the surface of the porous tube and the bulk phase. It is therefore preferred that the flow of gas through the first gas zone, i.e. annular zone 15 in FIG. 1, be maintained laminar when methane is the hydrocarbon feedstream fed to the reactor and carbon tetrachloride is the desired chlorinated hydrocarbon product. Of course, laminar flow may also be advantageously employed with other hydrocarbon feeds, e.g. ethane. As used herein, the term "laminar" is meant to define fluid flow conditions wherein the individual particles of fluid are flowing in an orderly manner in substantially straight lines parallel to the long axis of the first gas zone (i.e. annular zone 15 in FIG. 1), with substantially no bulk mixing. Thus, turbulent flow, in which the individual particles of fluid flow in an erratic manner which complete bulk mixing, is not preferred.

The working of the preferred porous tube reactor embodiment and, in particular, the importance of controlling the degree of turbulence in the first elongated gas zone wherein the chlorination reactions occur, may be more fully appreciated by the following theoretical explanation which is not, however, in any way intended to limit the applicability of this process.

Consider the following consecutive-competitive reactions, $$YZ + AX_{4-n}Y_n \xrightarrow{k_n} AX_{3-n}Y_{n+1} + XZ \tag{I}$$

wherein n is consecutively equal to 0, 1, 2 and 3, $k_n$ is the reaction rate constant for the n reactant, and Z, X, Y and Z represent atoms of carbon, hydrogen, chlorine and chlorine, respectively, for methane chlorination. Thus, the variables $X_{4-n}$ and $Y_n$ represent the number of atoms of hydrogen and chlorine, respectively, in the $AX_{4-n}$ reactant, e.g., $AX_4$ for n=0 or $AXY_4$ for n=3. According to Fouss (J. Am. Chem. Soc. 65, 2406 (1943)) and to Natta and Mantica (J. Am. Chem. Soc. 74, 3152 (1952)), the relative amounts of the products of consecutive-competitive reactions are dependent solely on the ratios of the reaction rate constants, $k_n$, and on the type of reactor, as will be shown by the following analysis.

Assuming that the rate of reaction of component $AX_{4-n}Y_n$ is directly proportional to its concentration, designated as $C_m$ (wherein m is an integer of from 0 to 4) then the time rate of change of concentration for each component is equal to the rate at which a component is formed minus the rate at which it is reacted. The relative rate of change of concentration is then found by dividing the expressions for $C_1$, $C_2$, $C_3$ and $C_4$ by that for $C_0$, thus eliminating time as a variable and leading to the following expressions:

$$\frac{dC_1}{dC_0} = K_5 \frac{C_1}{C_0} - 1 \tag{IIa}$$

$$\frac{dC_2}{dC_0} = K_6 \frac{C_2}{C_0} - K_5 \frac{C_1}{C_0} \tag{IIb}$$

$$\frac{dC_3}{dC_0} = K_7 \frac{C_3}{C_0} - K_6 \frac{C_2}{C_0} \tag{IIc}$$

$$\frac{dC_4}{dC_0} = -K_7 \frac{C_3}{C_0} \tag{IId}$$

wherein $K_5 = k_1/k_0$, $K_6 = k_2/k_0$ and $K_7 = k_3/k_0$, the ratios of the individual reaction rate constants.

As is evident from the foregoing, $C_0$ corresponds to the concentration of $AX_4$, $C_1$ corresponds to the concentration of $AX_3Y$, $C_2$ to the concentration of $AX_2Y_2$, and $C_3$ to the concentration of $AXY_3$ and $C_4$ to the concentration of $AY_4$.

Figure 4:
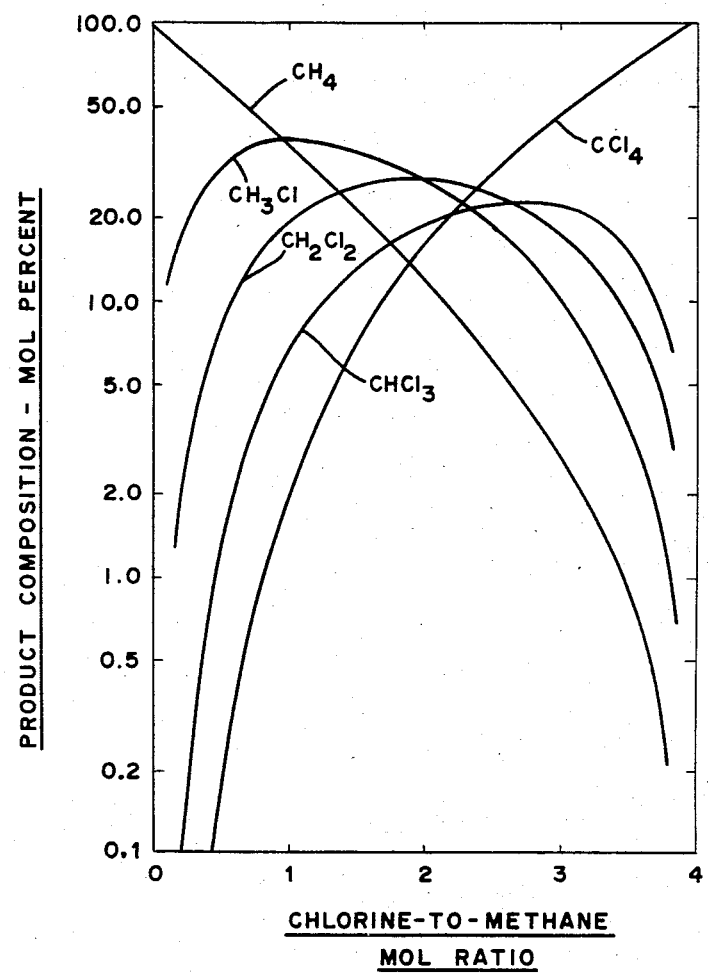
FIG. 4 is a plot of product composition vs. chlorine-to-methane mol ratio for methane chlorination in a tubular flow reactor.

For a tubular flow reactor equations IIa to IId can be integrated either analytically or numerically to give the composition of the reaction products. Product compositions for a feed consisting of pure $AX_4$ and reaction rate constant ratios of unity (i.e. $K_5 = K_6 = K_7 = 1$) are calculated from Equations IIa to IId as illustrated in FIG. 4, wherein $CH_4$ is the feed hydrocarbon, $CCl_4$ is the desired chlorinated product and $CHCl_3$, $CH_2Cl_2$ and $CH_3Cl$ are the partially-chlorinated intermediates.

In a back-mixed reactor the concentrations on the right side of equations IIa to IId are constant and equal to those of the exit stream (subscript e) and the derivatives on the left side of equations IIa to IId are replaced by the finite differences between the concentrations of the reactor exit stream and the reactor feed stream (subscript f), thus reducing the differential equations to the algebraic expressions IIIa to IIId, which have been arranged to solve for the concentrations of the exit stream:

$$C_{1e} = \frac{C_{0f} - C_{0e} - C_{1f}}{1 + K_5(Q-1)} \tag{IIIa}$$

$$C_{2e} = \frac{K_5(Q-1)C_{1e} + C_{2f}}{1 + K_6(Q-1)} \tag{IIIb}$$

$$C_{3e} = \frac{K_6(Q-1)C_{2e} + C_{3f}}{1 + K_7(Q-1)} \tag{IIIc}$$

$$C_{4e} = \frac{K_7(Q-1)C_{3e} + C_{4f}}{1} \tag{IIId}$$

wherein $Q = C_{0f}/C_{0e}$.

Figure 5:
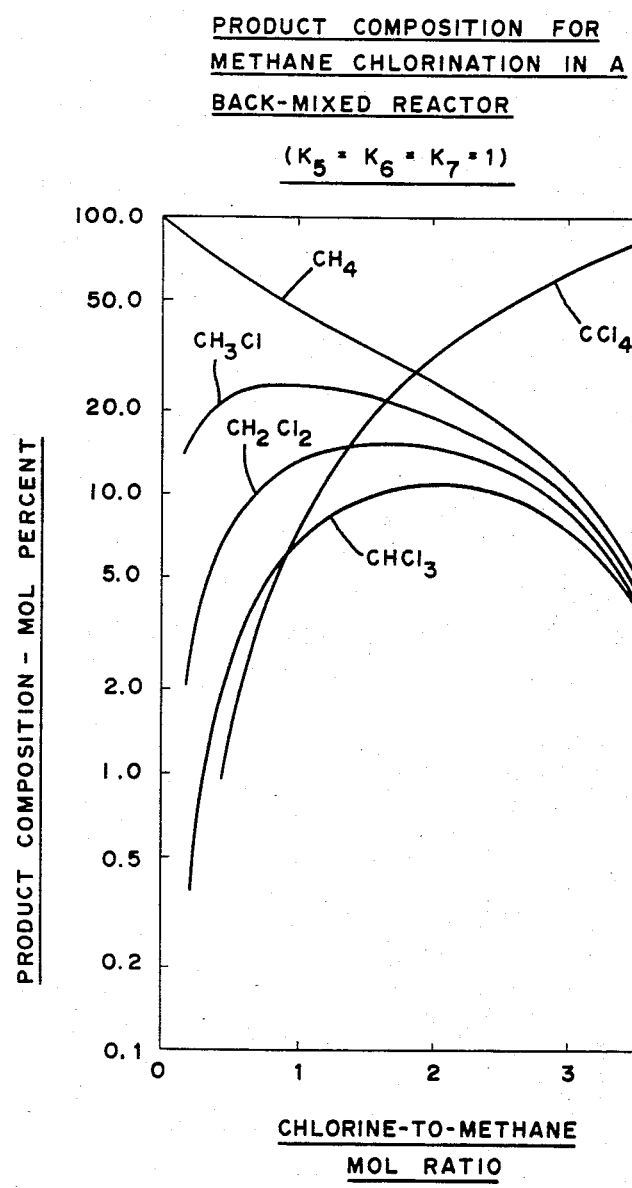
FIG. 5 is a plot of product composition vs. chlorine-to-methane mol ratio for methane chlorination in a back-mixed reactor.

FIG. 5 shows the product compositions for a feed consisting of the pure $AX_4$ and reaction rate constant ratios of unity (i.e., $K_5 = K_6 = K_7 = 1$) for the case of the back-mixed reactor, as calculated using Equations IIIa to IIId. It will be noted that the concentrations of the intermediate products (i.e., $CHCl_3$, $CH_2Cl_2$ and $CH_3Cl$) are somewhat lower in the back-mixed reactor than in the tubular flow reactor.

To compare the above results using a conventional back-mixed or tubular flow reactor with that obtained using an apparatus of the present invention, reference will be made to the preferred embodiment, the porous tube reactor illustrated in FIG. 1. Referring again to FIG. 1 for purposes of illustration, reactant $AX_4$ is introduced via line 5 into the upper end of annular zone 15 formed by porous tube 3 and outer tube 2. Reactant YZ is introduced into porous tube 3 at inlet 4 and is maintained at a pressure in excess of that in annular zone 15 for diffusion of YZ through porous tube 3 and into zone 15. The feed rate of reactant YZ to porous tube 3 is less than the amount stoichiometrically required for complete conversion of YA to $AY_4$ (i.e., less than 4 mols of YZ per mol of $AX_4$). The bulk flow in the longitudinal direction of annular zone 15 is laminar. The reaction products are withdrawn from annular zone 15 via line 6.

Figure 6:
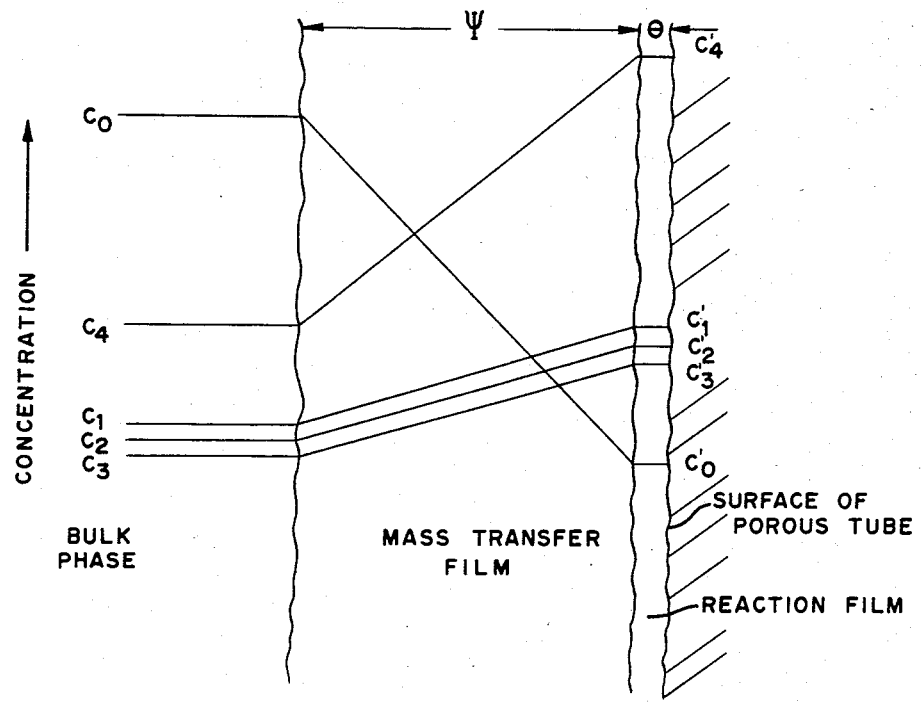
FIG. 6 is a theoretical representation of the bulk phase, mass transfer film and reaction film for laminar flow.

If we assume that the reaction is quite fast, then all the reaction can be regarded as taking place in a very thin film on the surface of the porous tube. This reaction film is assumed to be separated from the bulk phase in the annulus by a mass transfer film. Reactants $AX_{4-n}Y_n$ diffuse from the bulk phase through this mass transfer film to the reaction film while products $AX_{3-n}Y_{n+1}$ diffuse from the reaction film to the bulk phase. This is illustrated by FIG. 6, wherein $C_0$ to $C_4$ are concentrations in the bulk phase, $C_0'$ to $C_4'$ are concentrations in the reaction film, 0 is the thickness of the reaction film and $\Psi$ is the thickness of the mass transfer film.

The composition of the bulk phase will change in the longitudinal direction of flow as the reaction proceeds. It is assumed that the bulk phase constitutes by far the greatest part of the volume of the annulus.

When a molecule of reactant $AX_4$ diffuses to the reaction film on the surface of the porous tube it reacts to form $AX_3Y$. This molecule of $AX_3Y$ can either diffuse back into the bulk phase or it can react further to form, in turn, $AX_2Y_2$, $AXY_3$ and $AY_4$. The last product, $AY_4$, can react no further and hence can only diffuse back to the bulk phase.

The concentrations of the various components in the reaction film on the surface of the porous tube and in the bulk base depend on the relative rates of diffusion and reaction. If the diffusion rate is fast compared to the reaction rate, then the concentration of the various components will be the same in the reaction film and the bulk phase and the composition of products will be indistinguishable from that obtained with a tubular flow reactor. If the reaction rate is fast compared to the diffusion rate then the concentrations in the reaction film and bulk phase will be as shown by FIG. 6.

The equality between the mass flows across the mass transfer film and the reaction rates at the surface of the porous tube leads to the following expressions:

$$\frac{dC_1}{dC_0} = K_5 \frac{C_1'}{C_0'} - 1 = K_1 \frac{C_1 - C_1}{C_0 - C_0'} \quad \text{(IVa)}$$

$$\frac{dC_2}{dC_0} = K_6 \frac{C_2'}{C_0'} - K_5 \frac{C_1'}{C_0'} = K_2 \frac{C_2 - C_2}{C_0 - C_0'} \quad \text{(IVb)}$$

$$\frac{dC_3}{dC_0} = K_7 \frac{C_3'}{C_0'} - K_6 \frac{C_2'}{C_0'} = K_3 \frac{C_3 - C_3}{C_0 - C_0'} \quad \text{(IVc)}$$

$$\frac{dC_0}{dC_0} = K_7 \frac{C_3'}{C_0'} - 1 = K_4 \frac{C_4 - C_4}{C_0 - C_0'} \quad \text{(IVd)}$$

wherein $K_1$, $K_2$ and $K_3$ are defined to be the ratios of diffusivities $D_m$; $K_1 = D_1/D_0$, $K_2 = D_2/D_0$, $K_3 = D_3/D_0$ and $K_4 = D_4/D_0$; $C_m$ is the concentration of $AX_{4-n}Y_n$ in the bulk phase; and $C_m'$ is the concentration of $AX_{4-n}Y_n$ in the reaction film. As before, $D_0$ corresponds to the diffusivity of $AX_4$, $D_1$ to the diffusivity of $AX_3Y$, $D_2$ to the diffusivity of $AX_2Y_2$, $D_3$ to the diffusivity of $AXY_3$ and $D_4$ to the diffusivity of $AY_4$. In the diffusional process reactant $AX_4$ is assumed to be the predominant constituent of the mass transfer film.

From these relationships expressions for the concentrations at the surface of the porous tube can be developed:

$$C_1' = \frac{(1/K_1)RC_0' + C_1}{1 + (K_5/K_1)R} \quad \text{(Va)}$$

$$C_2' = \frac{(K_5/K_7)RC_1' + C_2}{1 + (K_6/K_2)R} \quad \text{(Vb)}$$

$$C_3' = \frac{(K_6/K_3)RC_2' + C_3}{1 + (K_7/K_3)R} \quad \text{(Vc)}$$

$$C_4' = (K_7/K_4)RC_3' + C_4 \quad \text{(Vd)}$$

wherein $$R = \frac{C_0 - C_0'}{C_0'} \quad \text{(VI)}$$

and is therefore the ratio of (1) the difference between the bulk phase concentration and reaction film concentration of methane to (2) the reaction phase methane concentration.

Considering only the concentration $C_0$, it is evident that $$\frac{D_0(C_0 - C_0')}{\Psi} = k_0 C_0' \quad \text{(VII)}$$

wherein $\Psi$ is as defined above.
Hence, $$R = \frac{k_0 \Psi}{D_0} \quad \text{(VIII)}$$

Thus, R can be regarded as constant for any given reactor at a particular set of temperature, pressure and gas flow rate conditions.

A large value of R (e.g., R>3) therefore implies that the reaction rate constant for $AX_4$ is large compared to the diffusion rate from the bulk phase into the reaction film. A large value of R can correspond to a large value of $k_0$ (reaction rate constant) and/or a large value of $\Psi$ (mass transfer film thickness) and/or a small value of $D_0$ (diffusivity). Under these circumstances the intermediate products formed will be further reacted to form predominantly $AY_4$ and thus lead to the suppression of the intermediate products which characterizes the porous tube reactor when operated in the laminar flow regime.

A small value of R (e.g., R<1) implies that the diffusion rate for $AX_4$ is large compared to the reaction rate. For the limiting case in which R=0, and hence in which the rate of diffusion is infinitely greater than the rate of reaction or the thickness of the mass transfer film is negligibly small, equations IVa to IVd reduce to those for the tubular flow reactor and the product composition from the porous tube reactor will be indistinguishable from that of the tubular flow reaction. One way of attaining a small value of R would be by inducing turbulence in the first elongated zone, e.g., in annular zone 15 in the porous tube reactor of FIG. 1, thus destroying the concentration difference between the surface of the porous tube and the bulk phase. This is equivalent to greatly increasing the value of $D_0$, the diffusivity of $AX_4$ or greatly decreasing the value of $\Psi$, the thickness of the mass transfer film.

Figure 7:
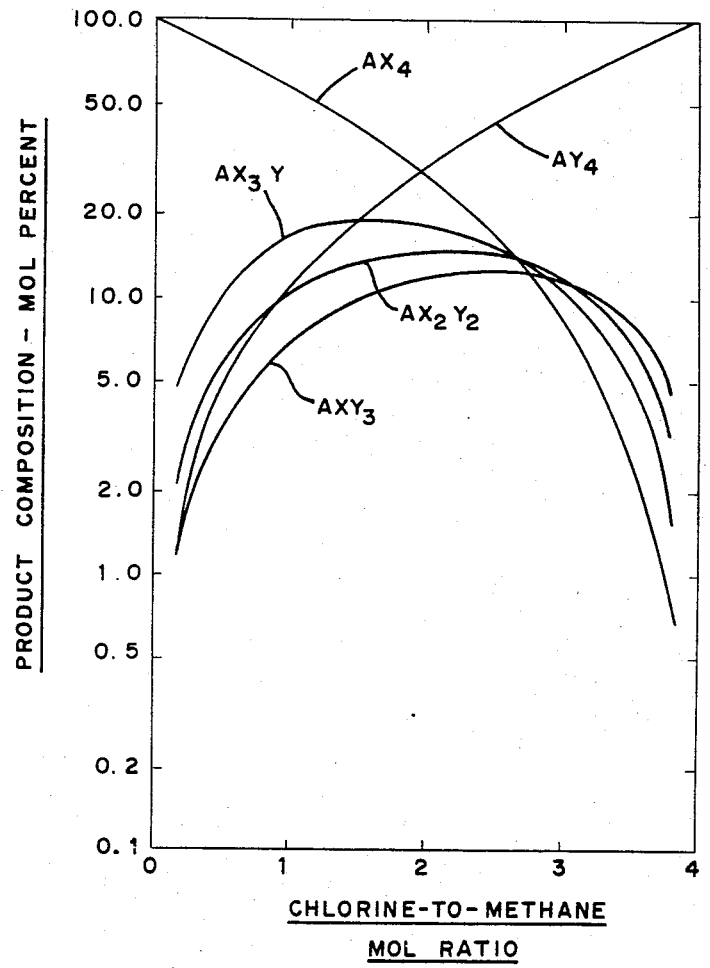
FIGS. 7, 8 and 9 are theoretical plots of product composition vs. chlorine-to-methane mol ratio for methane chlorination in a porous tube reactor with increasingly developed laminar flow (decreasing turbulence and bulk mixing).
Figure 8:
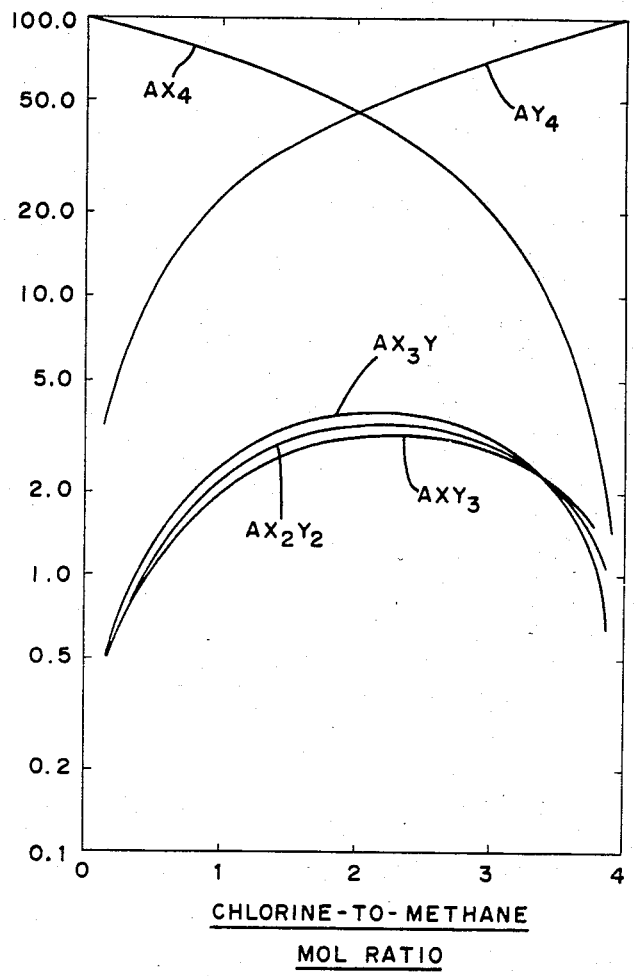
Figure 9:
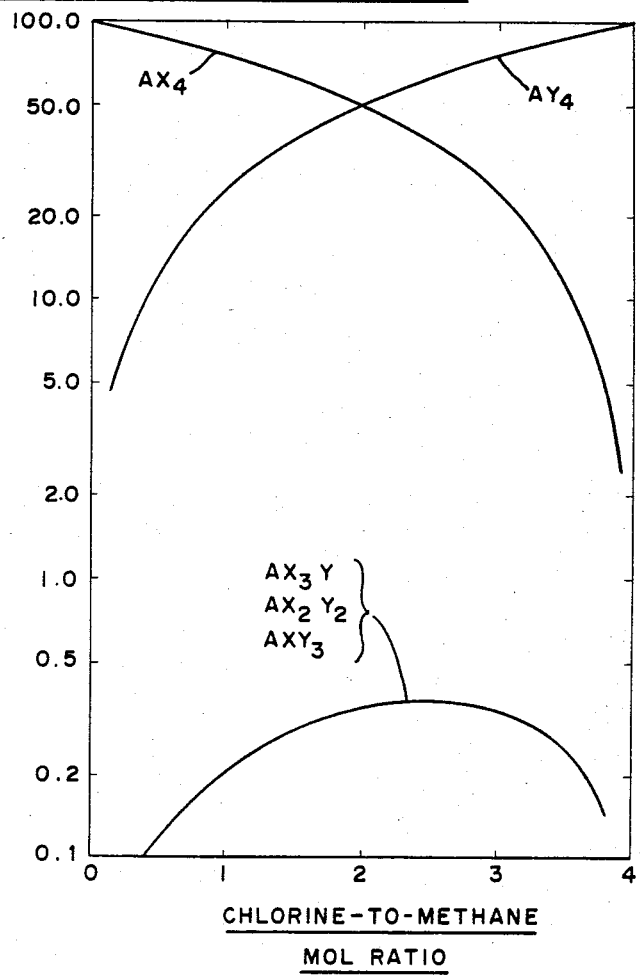
Figure 10:
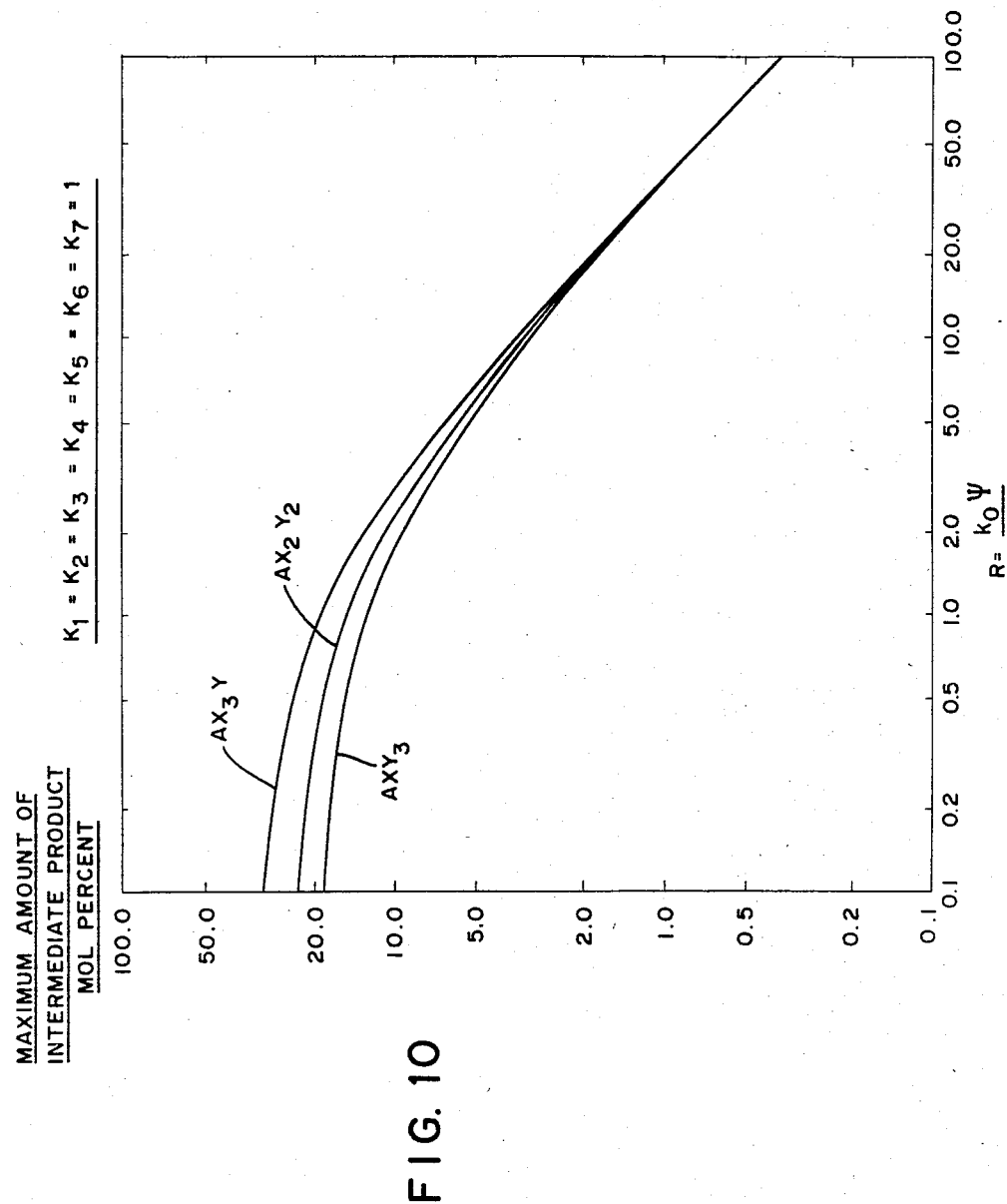
FIG. 10 is a plot of the effect of R-values (as defined below) on the maximum amount of intermediate partially chlorinated hydrocarbons for competitive, consecutive reactions using a porous tube reactor in FIG. 1.

FIGS. 7 through 9 show the product stream compositions calculated by numerical solution of the preceding equations IVa to Va to Vd for a feed consisting of pure $AX_4$, for values of R equal to 1, 9 and 99 in FIGS. 7–9, respectively. As R increases, it is evident that the concentrations of the intermediate products become progressively smaller. For example, the maximum concentration of $AX_3Y$ in an apparatus of the present invention using laminar flow through the first elongated gas zone (e.g., R=9 for the porous tube reactor discussed above) is about one-tenth of the value obtained from a tubular flow reactor (i.e., wherein R=0). The maximum concentration attained by each of the intermediate products as a function of R is shown by FIG. 10.

Thus, from this analysis, it can be seen that the apparatus of the present invention suppresses the formation of intermediate products of consecurive-competitive reactions when the flow of gas through the first elongated gas zone is in the laminar region and that the extent of this suppression depends on the value of R, which is a function of the reaction rate constant, diffusivity and mass transfer film thickness.

For the foregoing reasons, the process of the present invention is preferably characterized by an R of greater than about 1, more preferably at least about 5, in which R is as defined above in Equation VIII. While the above relationships (e.g., Equations IVa to VIII) were developed for porous tube reactors of the present invention, it should be understood that they are independent of geometry of the first and second elongated gas zones.

The chlorinated hydrocarbon produced in the apparatus in accordance with the present invention may be recovered from the gases exiting the reactor by conventional means, and a discussion of its recovery from these exit gases is not necessary here. Unreacted gas exiting the reactor may be recycled to the reactor for more complete chlorination where desired.

The apparatus of the present invention may be further illustrated by reference to the following examples.

In the case of Examples 1–3, the reactor used comprises a porous tube of fritted Pyrex glass, having a pore size in the 0.9 to 1.4 micron range. It is 23.8 cm long, 4.3 cm O.D. and arranged concentrically within an outer tube 6.5 cm I.D. which is jacketed. Molten sodium nitrate is curculated through the jacket at a rate and temperature sufficient to maintain the reaction in an isothermal condition at the temperature specified. The chlorine is introduced into the porous inner tube, the methane or ethane into one end of the annulus. The products of reaction are removed from the other end of the annulus and pass through a condenser at $-45°$ to $-50°$ C. The non-condensibles leaving the condenser are principally unreacted ethane or methane plus hydrogen chloride. In Examples 1–5 the flow rates and reactor dimensions were such that flow in the reaction zone (annulus) was well into the laminar regime; Reynold's numbers were in the range of 20 to 150. Product samples are analyzed in all examples by gas chromatography.

EXAMPLES 1 AND 2

These chlorinations are carried out with ethane as the raw material:

|  |  | Ex. 1 | Ex. 2 |
|---|---|---|---|
| Temperature |  | 360° C. | 360° C. |
| Chlorine Flow (gram mols/sec) $\times 10^4$: |  | 1.2 | 2.4 |
| Ethane flow (gram mols/sec) $\times 10^4$ |  | 1.2 | 0.6 |
| Ratio of $Cl_2/CH_3CH_3$ |  | 1:1 | 4:1 |
| Pressure abs. of $Cl_2$ in porous tube |  | 31–32" Hg. | 31–32" Hg. |
| Pressure abs. of $CH_3CH_3$ in annulus |  | 30" Hg. | 30" Hg. |
| Composition in liquid product (mole %) |  |  |  |
| Vinyl Chloride | $CH_2:CHCl$ | 2.4 | 0.0 |
| Ethyl Chloride | $CH_3CH_2Cl$ | 7.4 | 0.1 |
| Vinylidene Chloride | $CH_2:CCl_2$ | 13.1 | 2.9 |
| Ethylidene Chloride | $CH_3CHCl_2$ | 10.4 | 1.5 |
| Trans-Dichloroethylene Tr. | $CHCl:CHCl$ | 3.6 | 3.0 |
| Cis-dichloroethylene | $Cis.CHCl:CHCl$ | 6.3 | 4.5 |
| 1,2-Dichloroethane | $CH_2ClCH_2Cl$ | 0.5 | 1.3 |
| Methyl Chloroform | $CH_3CCl_3$ | 10.2 | 5.9 |
| Carbon Tetrachloride | $CCl_4$ | 1.1 | 0.5 |
| Trichloroethylene | $CHCl:CCl_2$ | 25.0 | 36.4 |
| Tetrachloroethylene | $CCl_2:CCl_2$ | 10.6 | 24.7 |
| 1,2,2,2-Tetrachloroethane | $CH_2ClCCl_3$ | 4.4 | 6.4 |
| Other |  | 6.1 | 13.3 |

Attention is called to the excellent yields of products trichloroethylene and tetrachloroethylene. It is instructive to contrast these results with those obtained by chlorination of ethane in a conventional tubular flow reactor by comparable temperature and pressure and with the same chloride to ethane ratio of 1:1 as for Example 1. According to McBee, et al., "Chlorination of Ethane", Industrial Engineering Chemistry, 41 No. 4, 799, at 802 (1949), the approximate composition of the liquid products would be (mol %):

| Vinyl Chloride ($CH_2:CHCl$) | 1 |
|---|---|
| Ethyl Chloride ($CH_3CH_2Cl$) | 75 |
| Ethylidene Chloride ($CH_3CHCl_2$) | 17 |
| 1,2,-Dichloroethane ($CH_2ClCH_2Cl$) | 7 |

Thus, while the conventional process leads predominantly to ethyl chloride and ethylidene chloride with negligible amounts of trichloroethylene and tetrachloroethylene, the process of this invention leads to much smaller amounts of ethyl chloride and ethylidene chloride and substantial amounts of trichloroethylene and tetrachloroethylene.

It is clear that this process using a porous tube reactor so designed as to operate under isothermal conditions, and controlled variables such as the degree of turbulence in the annular reaction zone, the temperature, the ratio of reactants, the feed rate and the pressure differential across the porous barrier, can provide effective control of the percentage composition of the chlorinated reaction products, thus the production of specific chlorinated products and groups of products in good yields can be obtained.

EXAMPLE 3

The conditions for this specific example in which methane is used as feed, are as follows:

| Temperature maintained |  | 350° C. |
|---|---|---|
| Chlorine flow (grams mols/sec) $\times 10^4$ |  | 1.4 |
| Methane flow (gram mols/sec) $\times 10^4$ |  | 1.4 |
| Ratio: $Cl_2/CH_4$ |  | 1.1 |
| Pressure abs. of $Cl_2$ in porous tube |  | 31–32" Hg. |
| Pressure abs. of $CH_4$ in annulus |  | 30" Hg. |
| Composition of liquid product (mole %): |  |  |
| Methyl chloride: | ($CH_3Cl$) | 11.4 |
| Methylene chloride: | ($CH_2Cl_2$) | 4.4 |
| Chloroform: | ($CHCl_3$) | 6.3 |
| Carbon tetrachloride: | ($CCl_4$) | 69.1 |
| Tetrachloroethylene: | ($CCl_2:CCl_2$) | 17.6 |

The high yield of the desired carbon tetrachloride will be noted.

EXAMPLE 4

In the following Example, a different reactor was used which comprised a porous tube of sintered alumina, having an average pore size of 60 microns. The porous tube is 60 cm long, 1.9 cm O.D. and arranged concentrically within an outer tube 6.25 cm I.D. which is equipped with a heating/cooling means so as to maintain the reaction in an isothermal condition at the temperature specified. The chlorine is introduced into the porous inner tube and the methane into one end of the annulus. The products of reaction are removed from the other end of the annulus and pass through a condenser at $-45°$ to $-50°$ C. The non-condensibles leaving the condenser are principally unreacted methane plus hydrogen chloride.

The conditions for this specific example are:

| Temperature maintained | 425° C. |
|---|---|

-continued

| Pressure abs. of Cl₂ in porous tube | 31–32" Hg. |
| Pressure abs. of CH₄ in annulus | 30" Hg. |

Several runs are made in which the $Cl_2/CH_4$ mole ratio in the feed is varied. These mole ratios and the composition of the product gas stream is set forth in Table I:

TABLE I

| Run No. | Cl₂:CH₄ Mole Ratio | Composition of Product Gas (Mole %) | | | |
|---|---|---|---|---|---|
| | | CH₃Cl | CH₂Cl₂ | CHCl₃ | CCl₄ |
| 1 | 0.67 | 5.0 | 18.1 | 29.1 | 47.6 |
| 2 | 1.74 | 4.1 | 16.5 | 31.3 | 47.4 |
| 3 | 2.14 | 4.0 | 12.4 | 26.0 | 55.8 |
| 4 | 2.76 | 2.2 | 5.3 | 13.4 | 70.1 |

The excellent yield of carbon tetrachloride and small quantity of by-products resulting from the use of the porous tube reactor may be compared with that obtained employing a conventional staged tubular flow reactor. Table II sets forth the tubular reactor data obtained by E. T. McBee, et al., in "Chlorination of Methane", *Industrial and Engineering Chemistry*, 34, No. 3, 296 at 298 (1942), employed the Hass-McBee chlorination process referenced in that article.

TABLE II

| | | Temperature: 440° C. | | | |
|---|---|---|---|---|---|
| Run No. | Cl₂:CH₄ Mole Ratio | CH₃Cl | CH₂Cl₂ | CHCl₃ | CCl₄ |
| 1 | 0.50 | 62.0 | 30.0 | 7.0 | 1.0 |
| 2 | 1.10 | 37.4 | 41.0 | 18.9 | 2.6 |
| 3 | 1.68 | 19.0 | 43.1 | 33.4 | 4.4 |
| 4 | 1.98 | 10.7 | 34.8 | 45.5 | 9.1 |
| 5 | 2.28 | 5.3 | 29.2 | 51.7 | 13.7 |
| 6 | 3.02 | 2.7 | 15.1 | 52.9 | 29.1 |
| 7 | 3.31 | — | 5.7 | 43.5 | 50.9 |
| 8 | 3.88 | — | — | 4.0 | 96.0 |

Thus, whereas use of a $Cl_2/CH_4$ mole ratio of 3.02 (Run 6) in the staged tubular flow reactor produced a product gas containing only 29.2 mole percent CCl₄, the porous tube reactor, employing a $Cl_2/CH_4$ mole ratio 8.6 percent *lower* (i.e., 2.76 mole ratio, run 4), achieved a product gas containing 70.1 mole percent CCl₄, for greater than a 58 percent improvement in the carbon tetrachloride content in the gas product. Moreover these greatly improved yields, and concomitant decreased by-products, are obtained using a lower temperature of reaction (425° vs. 440° C.).

EXAMPLE 5

Employing the porous tube reactor of Example 4, the following chlorinations are carried out with methyl chloride as the raw material, using the method of handling the reactants and products as employed with methane fed in Example 4:

| Temperature | 425° C. |
| Pressure abs. of Cl₂ in porous tube | 31–32" Hg. |
| Pressure abs. of CH₃Cl in porous tube | 30" Hg |

As in Example 4, several runs are made in which the $Cl_2/CH_3Cl$ mole ratio in the feeds are varied. The mole ratios employed and the composition of the product gases obtained are set forth in Table III.

TABLE III

| Run No. | Cl₂CH₃Cl Mole Ratio | Composition of Product Gas (Mole %) | | |
|---|---|---|---|---|
| | | CH₂Cl₂ | CHCl₃ | CHCl₄ |
| 1 | 0.67 | 49.9 | 27.7 | 22.2 |
| 2 | 1.74 | 26.6 | 32.5 | 39.4 |
| 3 | 2.14 | 11.1 | 20.9 | 64.4 |

The excellent CCl₄ yields and low by-product formation obtained using the porous tube reactor may be seen by reference to the data summarized in Table IV, which relates methyl chloride chlorination employing a staged tubular flow reaction as described in Bruce E. Kurtz, "Homogeneous Kinetics of Methyl Chloride Chlorination", *Industrial Engineering Chemical Process Design and Development*, Vol. 11, No. 3, 332, at 336 (1972).

TABLE IV

| | | Temperature: 460° C. | | |
|---|---|---|---|---|
| Run No. | Cl₂CH₃Cl Mole Ratio | Composition of Product Gas (Mole %) | | |
| | | CH₂Cl₂ | CHCl₃ | CHCl₄ |
| 1 | 0.5 | 77.5 | 20.0 | 2.5 |
| 2 | 1.0 | 62.1 | 33.3 | 4.5 |
| 3 | 1.5 | 36.2 | 46.8 | 16.4 |
| 4 | 2.0 | 21.0 | 47.4 | 31.6 |
| 5 | 2.5 | 4.0 | 38.4 | 57.6 |

Thus, the porous tube reactor produced a gas containing 64.4 mole percent CCl₄ using a $Cl_2/CH_3Cl$ mole ratio of only 2.14 (Run 3, Table III), whereas the 14 percent higher $Cl_2/CH_3Cl$ mole ratio of 2.5 (Run 5, Table IV) using the staged tubular flow reactor yielded a product gas containing only 57.6 mole percent CCl₄, which is over 10% less CCl₄ in the product.

In the above examples it is possible to determine values of R by inserting into Equations IVa to IVd and Va to Vd the actual values, known to those skilled in the art by reference to the published literature or by experimental determination by published techniques, for the reaction rate constant ratios ($K_5$ through $K_7$) and the diffusivity ratios $K_1$ through $K_4$) and calculating product composition curves of the type shown by FIGS. 7 to 9 by standard mathematical techniques, also known to those skilled in the art, for various values of R. The correct value of R is that value which corresponds to the product composition at a given chlorine-to-methane mol ratio which best agrees with the actual product composition obtained experimentally at the same chlorine-to-methane mol ratio. For example, employing the method described above to the results of Example 3 it is found that an R value of 9 gives a product composition which best agrees with the actual product composition of Example 3. Values of R corresponding to the results of the other examples can be calculated in the same fashion and will be found to be in the approximate range of 1 to 10.

EXAMPLE 6

Chlorination of isobutylene was carried out in the reactor of Example 4. With the exception that the porous tube was impregnated with a CuCl₂ catalyst (3–4% Cu). The reaction was carried out at 300° C. and at essentially 1 atm pressure. Chlorine was introduced through the porous tube and isobutylene to the annular space. The $Cl_2:C_4H_8$ ratio was 7:1. The products were primarily penta- and hexachlorinated isobutylene. Very little quatre- and almost no trichlorinated material left the reactor. Some chlorine fed was not reacted. Increasing the residence time would have reduced this.

EXAMPLE 7

Bromine is reacted with 2-octene in the same manner as is chlorine and isobutylene in Example 6. Highly brominated reaction products predominate.

EXAMPLE 8

Benzene is chlorinated in the apparatus described in Example 4 at a temperature of 500° C. The formation of mono-, di and trichloro benzenes is suppressed.

EXAMPLE 9

Xylene is brominated in the same manner as is found in Example 7 to produce highly brominated xylene.

EXAMPLES 10-12

Chlorine, fluorine and bromine are reacted with hexane in a similar manner to the above examples to yield highly substituted products with suppressed intermediate products.

Other modes of applying the principle of the invention may be employed instead of those explained, change being made as regards the apparatus, or compounds herein disclosed, provided the apparatus stated by any of the following claims, or the equivalent of said stated apparatus, be employed.

I claim:

1. A process for suppression of partially halogenated intermediates in isothermal consecutive competitive gas phase reaction which comprises:
   a. passing a first gas feed stream containing a carbon compound having labile hydrogen selected from the group consisting of straight and branched chain cyclic and acyclic alkanes and alkenes having no more than 12 carbon atoms, benzenes, alkenylbenzenes and alkylbenzenes having no more than 9 carbon atoms, their partially reacted intermediates and mixtures thereof under pressure into one end of a first elongated gas zone positioned within a substantially gas-impervious barrier;
   b. passing a second gas stream containing a member selected from the group consisting of $F_2$, $Cl_2$ and $Br_2$ under pressure into a second elongated gas zone positioned along said first zone, said first and second elongated gas zones being separated along the major length thereof by a porous member;
   c. maintaining the pressure of the second gas stream in the second gas zone in excess of the pressure in the first gas zone to allow flow of said second gas through the porous member;
   d. maintaining a Reynolds number $N_{Re}$ for stream in the first gas zone at a non-zero value less than about 2,000 to effect consecutive-competitive reaction between the first gas and the second gas, in a reaction film on the surface of the porous member facing the first zone for production of more highly halogenated product and to suppress diffsion of partially halogenated intermediates from said reaction film wherein the Reynolds number, $$N_{Re} = \frac{4A\bar{v}\rho}{P\mu}$$

wherein
   A = cross-sectional area of the first gas zone;
   P = total length of the perimeter of the cross-sectional area of first gas zone;
   $\bar{v}$ = average velocity of the gas stream in the first gas zone;
   $\rho$ = density of the gas stream in the first gas zone;
   $\mu$ = viscosity of the gas in the first gas zone; and
   e. withdrawing a gas stream containing the halogenated product from the other end of the first gas zone.

2. The process of claim 1 wherein the first elongated zone is substantially annular and is positioned inside a substantially gas-impervious housing, and wherein the second elongated gas zone is positioned internally within the porous member, said porous member comprising a porous tube closed at one end and positioned at the core of said annular first gas zone.

3. The process of claim 2 wherein the Reynolds Number is greater than 250.

4. The process of claim 2 wherein the Reynolds Number is greater than 500.

5. The process of claim 2 wherein the length to diameter of said annular gas zone is at least 10:1.

6. The process as described in claim 5 wherein $$\frac{4A}{P} = (D - d)$$

wherein
   D = the inner diameter of the gas-impervious housing
   d = the outer diameter of the porous member.

7. The process of claim 2 wherein the temperature is maintained in the range of 250° to 500° C.

8. The process of claim 1 wherein the second gas is fluorine.

9. The process of claim 8 wherein the first gas is straight and branched chain alkanes and alkenes of no more than 12 carbon atoms.

10. The process of claim 8 wherein the first gas is cyclopentane, cyclohexane or cyclohexene.

11. The process of claim 8 wherein the first gas is benzene, alkyl benzenes and alkenylbenzenes of no more than 9 carbon atoms.

12. The process of claim 1 wherein the second gas is chlorine.

13. The process of claim 12 wherein the first gas is straight and branched chain alkanes and alkenes of no more than 12 carbon atoms.

14. The process of claim 12 wherein the first gas is cyclopentane, cyclohexane or cyclohexene.

15. The process of claim 12 wherein the first gas benzene, alkylbenzenes and alkenylbenzenes of no more than 9 carbon atoms.

16. The process of claim 1 wherein the second gas is bromine.

17. The process of claim 16 wherein the first gas is straight and branched chain alkanes and alkenes of no more than 12 carbon atoms.

18. The process of claim 16 wherein the first gas is benzene, alkylbenzenes and alkenylbenzenes of no more than 9 atoms.

19. The process of claim 12 wherein alkanes and alkenes of between 3 and 12 carbon atoms are chlorinated in the presence of a catalyst.

20. The process of claim 12 wherein the first gas stream is isobutylene and a $CuCl_2$ catalyst is used.

21. The process of claim 16 wherein the alkanes and alkenes of between 3 and 12 carbon atoms are brominated in the presence of a catalyst.

* * * * *